United States Patent [19]

Sato et al.

[11] Patent Number: 5,125,740
[45] Date of Patent: Jun. 30, 1992

[54] METHOD AND APPARATUS FOR MEASURING OPTICAL CONSTANTS OF A THIN FILM AS WELL AS METHOD AND APPARATUS FOR FABRICATING A THIN FILM UTILIZING SAME

[75] Inventors: Hidemi Sato; Yasuo Hira; Atsuko Fukushima; Hiroshi Asao; Kazumi Kawamoto; Kenchi Ito; Ryuichi Funatsu, all of Yokohama, Japan

[73] Assignee: Hitachi, Ltd., Tokyo, Japan

[21] Appl. No.: 480,649

[22] Filed: Feb. 15, 1990

[30] Foreign Application Priority Data

Mar. 17, 1989 [JP] Japan ................................ 1-63601

[51] Int. Cl.$^5$ ............................................. G01N 21/41
[52] U.S. Cl. .................................. 356/128; 356/135; 356/137
[58] Field of Search ............................ 356/128–132, 356/73.1, 380–382

[56] References Cited

U.S. PATENT DOCUMENTS

| | | | |
|---|---|---|---|
| 3,645,631 | 2/1972 | Gupta | 356/136 |
| 3,746,450 | 7/1973 | Smith, Jr. | 356/135 |
| 3,770,352 | 11/1973 | White | 356/136 |
| 3,873,209 | 3/1975 | Schinke et al. | 356/135 |
| 4,746,179 | 5/1988 | Dahne et al. | 356/133 |

FOREIGN PATENT DOCUMENTS

| | | | |
|---|---|---|---|
| 58-75046 | 5/1983 | Japan . | |
| 0236004 | 11/1985 | Japan | 356/137 |
| 0144239 | 6/1988 | Japan | 356/137 |

OTHER PUBLICATIONS

"Light Waves in Thin Films and Integrated Optics", *Applied Optics*, vol. 10, No. 11, (1971), pp. 2395–2413.

*Primary Examiner*—Richard A. Rosenberger
*Assistant Examiner*—Hoa Pham
*Attorney, Agent, or Firm*—Fay, Sharpe, Beall, Fagan, Minnich & McKee

[57] ABSTRACT

A sample is located so as to be close to a prism and a light beam coming from a light source is projected to the prism while varying the incident angle to the prism as a parameter. The incident light beam to the prism is propagated therein and light emerging from the bottom surface of the prism, which is in contact with the sample, is projected to the sample. At the same time the intensity of light reflected by the bottom surface of the prism is measured. Optical constants such as the refractive index, the film thickness, the distribution of the refractive index, etc. are obtained by calculation, starting from measured values thus obtained.

13 Claims, 9 Drawing Sheets

METHOD FOR MEASURING PROPAGATION LOSS

PRINCIPLE OF MEASUREMENT

FIG. 8A

$$P_3 = \gamma P_0 e^{-\alpha x} \quad —(11)$$

FIG. 8B $$P_3' = \gamma(P_0 e^{-\alpha x_2} - P_2) \times e^{-\alpha(x_3 - x_2)} \quad —(12)$$

FIG. 8C $$P_3'' = \gamma(P_0 e^{-\alpha x_2'} - P_2') \times e^{-\alpha(x_3 - x_2')} \quad ----(13)$$

USING EQs. (1),(2) AND (3)

$$\alpha = \frac{\ln[P_2'(P_3 - P_3')/P_2(P_3 - P_3'')]}{x_2 - x_2'}$$

$\gamma$ : COUPLING COEFFICIENT OF PRISM 3
$\alpha$ : PROPAGATION LOSS IN THIN FILM
$P_0$: POWER OF LIGHT GUIDED BY THIN FILM

METHOD AND APPARATUS FOR MEASURING OPTICAL CONSTANTS OF A THIN FILM AS WELL AS METHOD AND APPARATUS FOR FABRICATING A THIN FILM UTILIZING SAME

BACKGROUND OF THE INVENTION

The present invention relates to a method and an apparatus for measuring optical constants of a thin film, and in particular to a simple method for measuring them with a high precision in a non-destructive manner. It relates further to an optical integrated circuit or a semiconductor element fabricated by feeding back measured values of the optical constants obtained by the measuring method stated above to the fabrication process for making the thin film.

Heretofore, as methods for measuring optical constants of a thin film, there are well known 1). ellipsometry, 2) interference microscopic method, etc. At first, the ellipsometry has a drawback that for relatively thick films ($\lesssim 0.300$ nm) the rafractive index cannot be determined quantitatively, unless the film thickness is known in some degree, because there exist periodical solutions in measured values. Further, measurement precision of the refractive index is in general as low as about $1 \times 10^3$. Still further, this method has another drawback that it cannot be applied for measuring the distribution of the refractive index.

Next, for the interference microscopic method it is necessary to slice measured medium and in addition to polish it optically. Therefore a long time is required for preparing a sample therefor. Further, since it is a destructive examination method, it has still another drawback that the sample cannot be reproduced. Still further, in the case where a Michelson interferometer etc. are used, since a product of refractive index and film thickness, i.e. optical path is obtained as a measured value, this method has still another drawback that it is useful only under a presumption that either one of them is known.

On the other hand, recently, with developing research on the semiconductor laser, research is actively performed on the optical integrated circuit, in which light receiving/emitting elements such as semiconductor laser devices, etc. and various sorts of waveguide type optical elements are integrated on one substrate. One of the most basic constituent elements of this optical integrated circuit is an optical waveguide. As a method for measuring the effective refractive index of the optical waveguide the prism coupler method is generally widely known, as discussed in Applied Optics, Vol. 10, No. 11 (1971), pp. 2395-2413, etc.

In the prior art technique described above a prism having a refractive index $n_p$ is disposed closely to an optical waveguide, putting an air layer therebetween. Then a light beam is projected to the bottom face of the prism with a predetermined angle of $\theta_p$ to excite guided light by matching it in the phase with the optical waveguide as the guided light is taken out to the exterior by means of a second prism. In this case, the effective refractive index of the optical waveguide can be calculated according to the principle that the angle of the emerging light beam varies depending on the guided mode in the optical waveguide. However, by the present method, since the bottom surface of the prism is plane, the coupling efficiency is small and further, since at least 2 prisms are necessarily used, the S/N ratio is lowered. Therefore the present method has still another drawback that no measurement can be effected with a high precision. In addition, in the case where the refractive index of the optical waveguide varies continuously, it has still another drawback that it cannot be used. Furthermore, in the case where it is applied for measuring propagation loss of the optical waveguide, fluctuations in the coupling efficiency are great and therefore there is a problem that it is not practical.

Consequently there was known heretofore no method for measuring the refractive index, which is one of the basic parameters of the optical integrated circuit, with a high precision, and it as necessary to perform the optimization by trial and error in the course of the fabrication of elements.

Further, in fabrication steps of the semiconductor element, in order to assure the reliability of the semiconductor element, it is an extremely important problem to evaluate and control in-situ the physical properties of various sorts of dielectric thin films made of $SiO_2$, $Si_3N_4$, PSG, etc., which are used as chip passivation films or interlayer insulating layers in the multi-layered wiring, at forming the film.

Heretofore the main monitoring device used in thin film fabrication steps was a film thickness meter. Consequently there was a drawback that it is impossible to measure the physical properties at the film formation to feedback them for optimizing the film formation conditions.

In the present specification the term "thin film" should be interpreted in a broad sense. The thin film may be a conductive film (metallic thin film, etc.), a dielectric thin film (optical waveguide, glass, SiN, LiNbO$_3$, etc.), a semiconductor thin film (Si, Ge, GaAs, etc.), or a macromolecular thin film (passivation film made of photosensitive resin, polyimide resin, etc.). The thin film may be formed by the sputtering method, the vacuum evaporation method, the CVD method the ion plating method, the thermal oxidation method, etc. The thin film may be a layer formed continuously on an original surface of a substrate by any method such as ion plating, etc. by using constituent materials working as an optical waveguide in an optical integrated circuit, a semiconductor element or an optical element.

SUMMARY OF THE INVENTION

An object of the present invention is to measure optical characteristics of a thin film such as refractive index, film thickness, distribution of refractive index, propagation loss, etc. with a high precision.

Another object of the present invention is to measure the optical characteristics described above in a simple non-destructive manner.

Still another object of the present invention is to provide an optical element having excellent properties, including a thin film formed with a high precision.

An optical measuring apparatus according to the present invention consists of a light source, a prism disposed closely to a sample, and a light receiving device for detecting light reflected by the bottom face of the prism. According to the present invention the relation between the incident angle of an incident light beam coming from the light source to the prism and the intensity of the light reflected by the bottom face of the prism is measured continuously while varying the incident angle by means of a prism formed in one body with a photodetector. Effective refractive indices of the medium (optical thin film, optical waveguide), the number of which refractive indices corresponds to the variables described above, are calculated by using the relation stated above between the incident angle of the incident light beam and the intensity of the light reflected by the bottom face of the prism. Here it is necessary to calculate at least two effective refractive indices for at least two incident angles. In the measurement stated above the coupling efficiency is increased by working the bottom surface of the prism in a spherical surface and in this way the measurement precision is improved. The intensity of the reflected light is measured for at least two values of a variable (incident angle) and the refractive index and the film thickness are determined simultaneously quantitatively by a numerical calculation. In the case where the refractive index is distributed, the distribution of the refractive index can be obtained by the inverse WKB method.

In the method for measuring the optical constants described above the measurement precision of e.g. the refractive index varies, approximately depending on the measurement precision of the incident angle of the beam. That is, the measurement precision of the refractive index being denoted by $\Delta N$, it can be given by $$\Delta N = \frac{\partial N}{\partial n_p} \Delta n_p + \frac{\partial N}{\partial a} \Delta a + \frac{\partial N}{\partial \theta_p} \Delta \theta_p$$

where $\Delta n_p$, $\Delta a$ and $\Delta \theta_p$ represent measurement errors of the refractive index of the prism, the vertex angle of the prism and the incident angle of the laser light beam to the prism, respectively. In the case where it is supposed that $\Delta n_p = 1 \times 10^{-5}$, $\Delta a = 0.5$ seconds and the incident angle is measured with a precision of $\Delta \theta_p = \pm 3$ seconds, the refractive index can be obtained in principle with an extremely high precision, which is as high as $1 \times 10^{-5}$. Consequently, according to the present invention, it is possible to measure the optical constant as monitors for the process of the formation of various sorts of thin films, which are fed back for optimizing the film fabrication conditions. Further, if two other prisms are added thereto, the present method can be applied for measuring the propagation loss in the optical waveguide. In this case, since the third prism is used as a monitor, an effect can be obtained that the coupling efficiency has no influences on the precision of the measurement of the loss, even if the second prism is moved.

By applying the measuring method according to the present invention to thin film formation methods such as sputtering, vacuum evaporation, CVD (Chemical Vapor Deposition), ion plating, etc., the controllability of the properties if the thin film thus formed is improved and thus it is possible to provide optical elements, optical integrated circuits and semiconductor elements of high performance.

DESCRIPTION OF THE PREFERRED EMBODIMENTS

Hereinbelow the preferred embodiments of the present invention will be explained in detail.

EMBODIMENT 1

Figure 1:
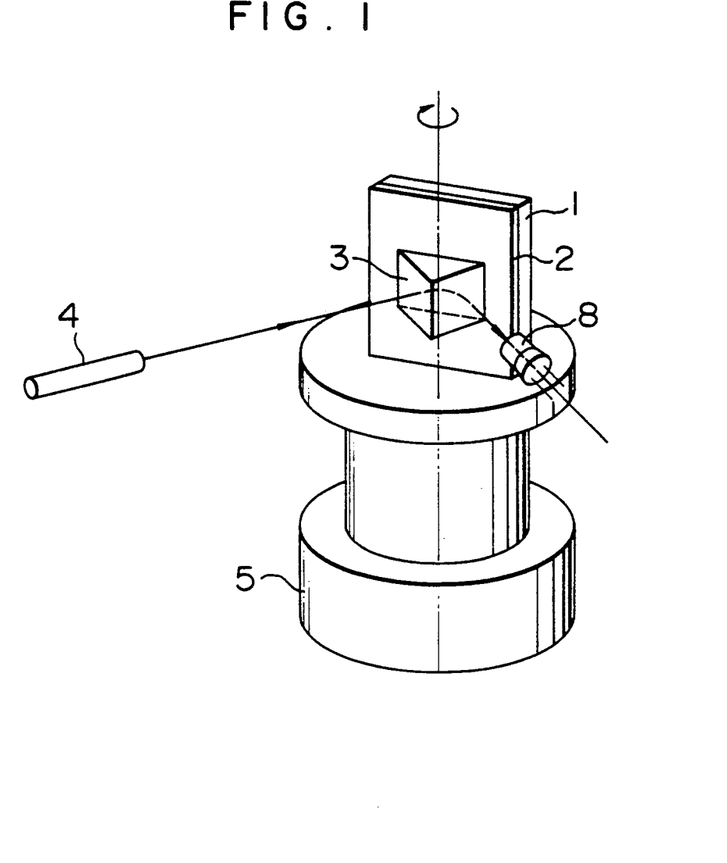
FIG. 1 is a perspective view illustrating an embodiment of the apparatus for measuring the optical constants of a thin film according to the present invention.
Figure 2:
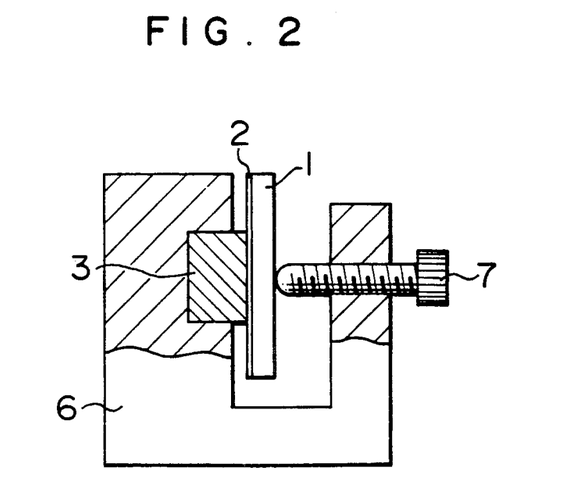
FIG. 2 is a cross-sectional view illustrating an example of the method for holding the prism.

FIG. 1 shows an embodiment of the present invention, which is an example of the measurement of the distribution of the refractive index in an optical waveguide 2, in which the refractive index varies continuously along the depth direction cf a substrate 1, which is e.g. an LiNbO$_3$ crystal. The optical waveguide 2 is prepared by thermally diffusing metal Ti. It is prepared under the following conditions After Ti has been deposited on the substrate 1 by the sputtering method to a thickness of 100 nm, it is diffused for 20 hours in an O$_2$ atmosphere at a temperature of 1000° C. Then a prism 3, whose bottom surface is worked in a spherical form, is closely disposed through an air layer to the optical waveguide 2. The optical coupling efficiency between the optical waveguide 2 and the prism 3 is increased by working the bottom surface thereof in the spherical shape. The radius of curvature is suitably comprised between 150 and 400 nm. Here a prism 3 made of TiO$_2$ (rutile) is used, which has a vertex angle of 55°, a refractive index $n_p = 2.854$ and a radius of curvature of the bottom surface of 250 nm. The projection of the light beam to the prism 3 is effected by using e.g. a He-Ne laser having a wavelength of 0.633 μm as the light source 4 and the incident angle is regulated by means of a rotating table 5 having ar accuracy of 0.5 seconds driven by a driving device, e.g. a pulse motor (not shown in the figure). FIG. 2 shows an example of the method for holding the prism 3. The prism 3 is secured to a holder 6 and the closeness thereof to the substrate 1 is regulated by means of a thrusting screw 7. The driving device may be controlled by a computer (not shown in the figure).

Figure 3A:
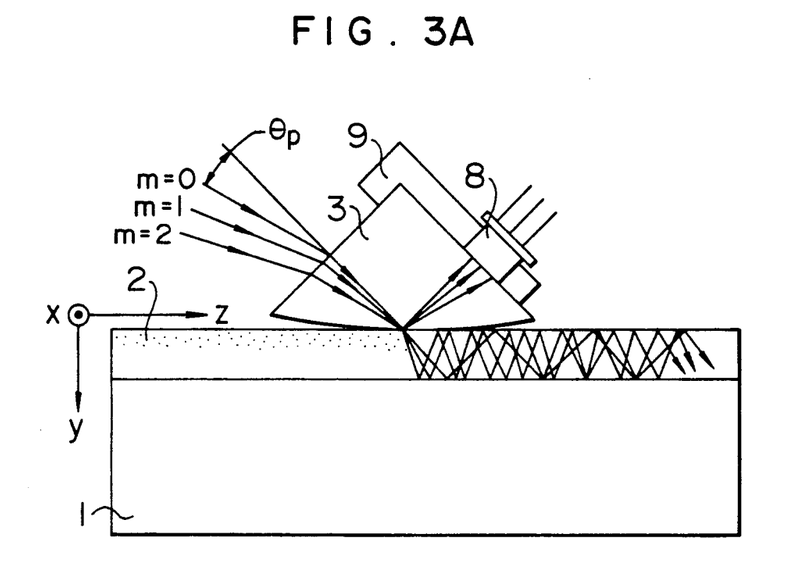
FIG. 3A is a scheme for explaining the trajectory of the light beam propagating through the prism to the medium in an embodiment of the present invention.

FIG. 3A indicates trajectories of light beams propagating in the optical waveguide 2 and reflected by the bottom surface of the prism, when the light beam is projected to the prism 3 with various incident angles. Here, as described previously, the light beams propagating in the optical waveguide have discrete values m (mode number) =0, 1, 2, . . . for the incident angle. In this way the incident angle of the light beam and the intensity of light reflected by the bottom surface are measured continuously by means of a photodetector 8. The light photodetector 8 and the prism 3 may be formed in one body by means of a holding member 9.

Now the principle of the measurement will be explained, referring to FIG. 3A.

In the case where the refractive index $n_f$ and the film thickness h of the thin film (optical waveguide) 2 formed on the substrate (refractive index $n_S$) are measured, the prism formed in one body with the photodetector, whose bottom surface is worked in a spherical surface, is disposed closely to the thin film 2 and a laser light beam is projected to the prism. Further the incident angle $\theta_p$ is varied and the incident angle $\theta_p$, for which the intensity of light reflected by the bottom surface of the prism is minimum, is read out. The effective refractive index N corresponding to the propagation mode is calculated by using Eq. (1);

$$N = \sin \alpha \sqrt{n_p^2 - \sin^2 \theta_p} + \cos \alpha \cdot \sin \theta_p \quad (1)$$

where
  α: vertex angle of the prism, and
  $n_p$: refractive index of the prism The material for the prism used here should be suitably selected, depending on the refractive index of the thin film to be measured. BK-7 glass ($n_p$=1.52), GGG ($n_p$=1.965), TiO$_2$ ($n_p$=2.584), GaP ($n_p$=3.314), etc. may be used as the material for the prism.

Next, by substituting N in the following eigenvalue equations (2) of the waveguide mode deduced from the Maxwell wave equations;

$$k_x h = (m + 1)\pi - \tan^{-1}\frac{k_x}{\gamma_s} - \tan^{-1}\frac{k_x}{\gamma_c} \quad (2)$$

where m: mode number, m=0, 1, 2, ; . .
  $k_x$, $\gamma_s$, $\gamma_c$: propagation constants of the laser light beam along the incident direction, $$\gamma_c = k_0 \sqrt{N^2}, \quad (3)$$

$$k_x = k_0 \sqrt{n_f^2 - N^2},$$

$$\gamma_s = k_0 \sqrt{N^2 - n^2},$$

wave number $k_0 = 2\pi/\lambda$, and
  λ: wavelength
by the right member of Eq. (1), and by solving the simultaneous equations (2), the refractive index $n_f$ and the film thickness h are calculated.

Figure 3B:
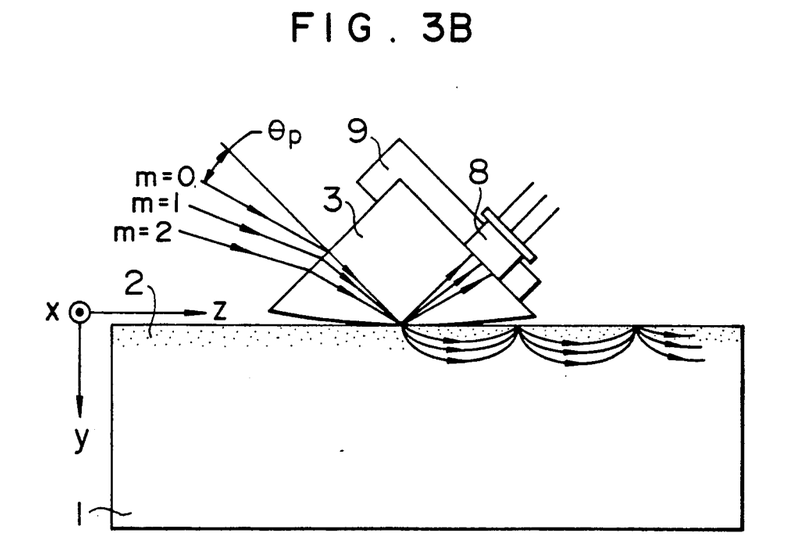
FIG. 3B is a scheme for explaining the trajectory of the light beam propagating through the prism to the medium, in which the refractive index varies continuously, in another embodiment of the present invention.

Next the case where the refractive index varies continuously in the direction of the depth of the medium, will be explained, referring to FIG. 3B. In FIG. 3B, an optical waveguide 2, in which the refractive index varies continuously, is formed in the upper portion of a substrate 1. A light beam propatating in this optical waveguide 2 traces an arc-shaped trajectory, which changes, depending on the propagation mode. Thereafter, the effective refractive index N corresponding to the propagation mode is calculated by using Eq. (1), just as described previously.

Now, the wave equations representing the TE mode in a two-dimensional optical waveguide, in which the distribution of the refractive index can be expressed by n(y), can be expressed, as follows, starting from the Maxwell equations;

$$\frac{\partial^2 Ex}{\partial x} + \{k_0^2 n^2(y) - \beta^2\} Ex = 0 \quad (4)$$

$$Hy = \frac{\beta}{\omega\mu_0} Ex \quad (5)$$

$$H_z = \frac{1}{j\omega\mu_0} \frac{\partial Ex}{\partial y} \quad (6)$$

where
  β: propagation constant in the x-direction,
  $\mu_0$: permeability in vacuum, and
  ω: angular frequency of light.

Using the effective refractive index N, Eq. (4) can be rewritten into:

$$\frac{\partial^2 Ex}{\partial y^2} + k_0 \{n^2(y) - N^2\} Ex = 0 \quad (7)$$

If n(y) is known, it is an eigenvalue problem to obtain an equivalent refractive index satisfying Eq. (7). Here, by the WKB approximation method, a following eigenvalue equation is obtained:

$$k_0 \int_0^{y_{tm}} \sqrt{n^2(y) - N_m^2} \, dy = \quad (8)$$

$$\left(m - \frac{3}{4}\right)\pi + \tan^{-1}\left[\frac{N^2_m - 1}{n_0^2 - N^2_m}\right]^{\frac{1}{2}}$$

$$m = 1, 2, \ldots$$

where
  $y_{tm}$: transition point of the mode of m-th order, and
  $m_0$: refractive index of the surface portion.

The inverse WKB method is a method, by which, starting from refractive indices $N_1$, $N_2$, ———, $N_m$ for different propagation modes, transition points $y_{t1}$, $y_{t2}$, ———$y_{tm}$ therefor are calculated to obtain a series of points (Nt$_1$, yt$_1$), (Ntm, y$_{tm}$). Connecting this series of points, it is possible to obtain the distribution of the refractive index.

Further, in the case where the refractive index of the substrate is greater than that of the thin film, called generally leaky mode, it is possible to obtain the refractive index $n_f$ of the thin film and the film thickness h from the following simultaneous eigenvalue equations:

$$N = n_f - \frac{\pi^2(m+1)^2}{2n_f(K_0h)^2} \quad (9)$$

Figure 4:
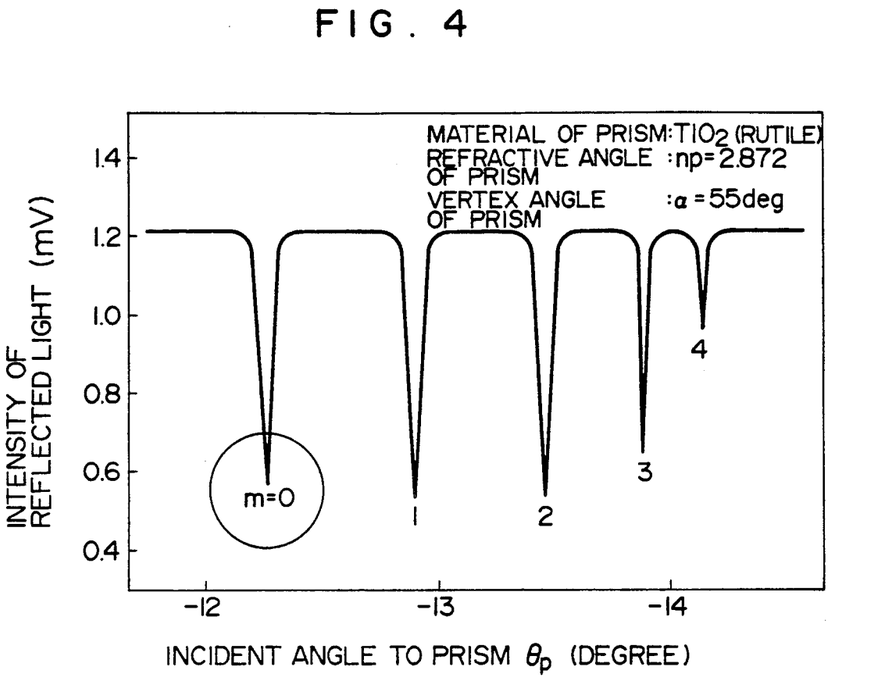
FIG. 4 is a graph showing the relation between the incident angle to the prism and the intensity of the reflected light obtained by means of a photodetector by the measuring method according to the present invention.

FIG. 4 shows an example of the measured data, in which the abscissa represents the incident angle $\theta_p$ of the light beam to the prism and the ordinate the intensity of the reflected light measured by the photodetector. In the figure each incident angle, for which the intensity of the reflected light is minimum, corresponds to the effective refractive index $N_m$ of a propagation mode (m=0, 1, 2, ———), which is calculated by using Eq. (1). Then, by using the measured data $N_m$ of the effective refractive index corresponding to the propagation mode described above, the series of points of the effective refractive index and the transition point are calculated by using Eq. (8). Table 1 shows calculated results of the refractive index and the transition point.

Figure 5:
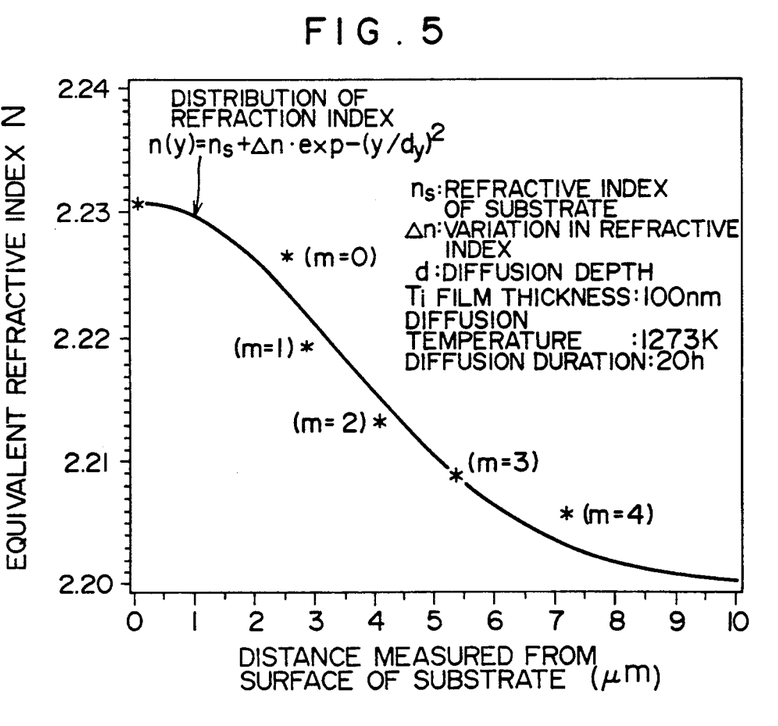
FIG. 5 is a graph showing characteristics of the distribution of the refractive index obtained by the method according to the present invention.

Further, when the effective refractive index $N_m$ and the transition point, i.e. the distance x measured from the surface of the substrate, indicated in Table 1 are plotted, *s indicated in FIG. 5 are obtained. Next supposing according to the diffusion theory that the distribution of the refractive index in the diffusion optical waveguide 2 is a Gauss distribution, and effecting curve fitting, the curve indicated by a full line in FIG. 5 is obtained. The distribution of the refractive index n(y) can be expressed by:

$$n(y) = n_2 + \Delta n \cdot exp - (y/dy)^2 \quad (10)$$

where
 $n_s$: refractive index of the substrate,
 $\Delta n$: variation in the refractive index, and
 dy: diffusion depth.

As indicated in Table 1, results of the analysis and predicted values by the diffusion experiment are in good accordance with each other both for the refractive index $n_0$ at the surface portion and for the diffusion depth dy. Further the theoretical curve (full line) in FIG. 5 corresponds well to the calculated values *. Thus the validity of the present method was able to be verified.

Furthermore the reproducibility in repeated measurements was found also to be as good as $3\sigma = 0.001$.

the light source, as applications other than the metal diffusion type optical waveguide.

EMBODIMENT 2

Next an example of measurement of the refractive index and the film thickness of a $TiO_2$ thin film used on an optical waveguide as a loaded layer for controlling light wave in the formation of optical integrated circuits will be explained. A substrate 1 made of BK-7 glass was used and a $TiO_2$ layer was formed thereon by the reactive sputtering method. In order to control the composition of the $TiO_2$ thin film, the sputtering was effected while adding $O_2$ gas to Ar gas. Table 2 shows measurement results of $n_f$ and h of thin films prepared while varying the partial pressure ratio of $O_2/Ar$ as a sputtering condition. As the result, a remarkable correlation between the $O_2/Ar$ partial pressure ratio and $n_f$ is found. Therefore it is possible to try to stabilize the film formation process by monitoring the value of $n_f$ at the film formation and by feeding it back to the film formation conditions.

TABLE 2

| Sample No. | Sputtering condition ($O_2/Ar$ partial pressure ratio) | Mode m | Incident angle $\theta_P$ | Refractive index $n_f$ | Film thickness h (μm) |
|---|---|---|---|---|---|
| 1 | 0 | 0 | 3°9'24" | 2.444261 | 4.865 |
|   |   | 1 | −14°52'56" |   |   |
| 2 | 0.1 | 0 | 7°37'30" | 2.532291 | 3.401 |
|   |   | 1 | −24°34'31" |   |   |
| 3 | 0.3 | 0 | 8°34'6" | 2.543894 | 3.352 |
|   |   | 1 | −24°27'58" |   |   |
| 4 | 0.5 | 0 | −10°19'9" | 2.562754 | 3.289 |
|   |   | 1 | −23°54'55" |   |   |

As the monitoring methods described above there are known 1) sampling examination, 2) method, by which a monitoring chamber is disposed in the vacuum chamber, in which samples are introduced appropriately and the measurement is effected in-process. Further the method described above can be applied to various sorts of thin film formation methods such as the vacuum evaporation method, the CVD method as well as to various sorts of thin films fabricated by using them.

EMBODIMENT 3

Figure 6:
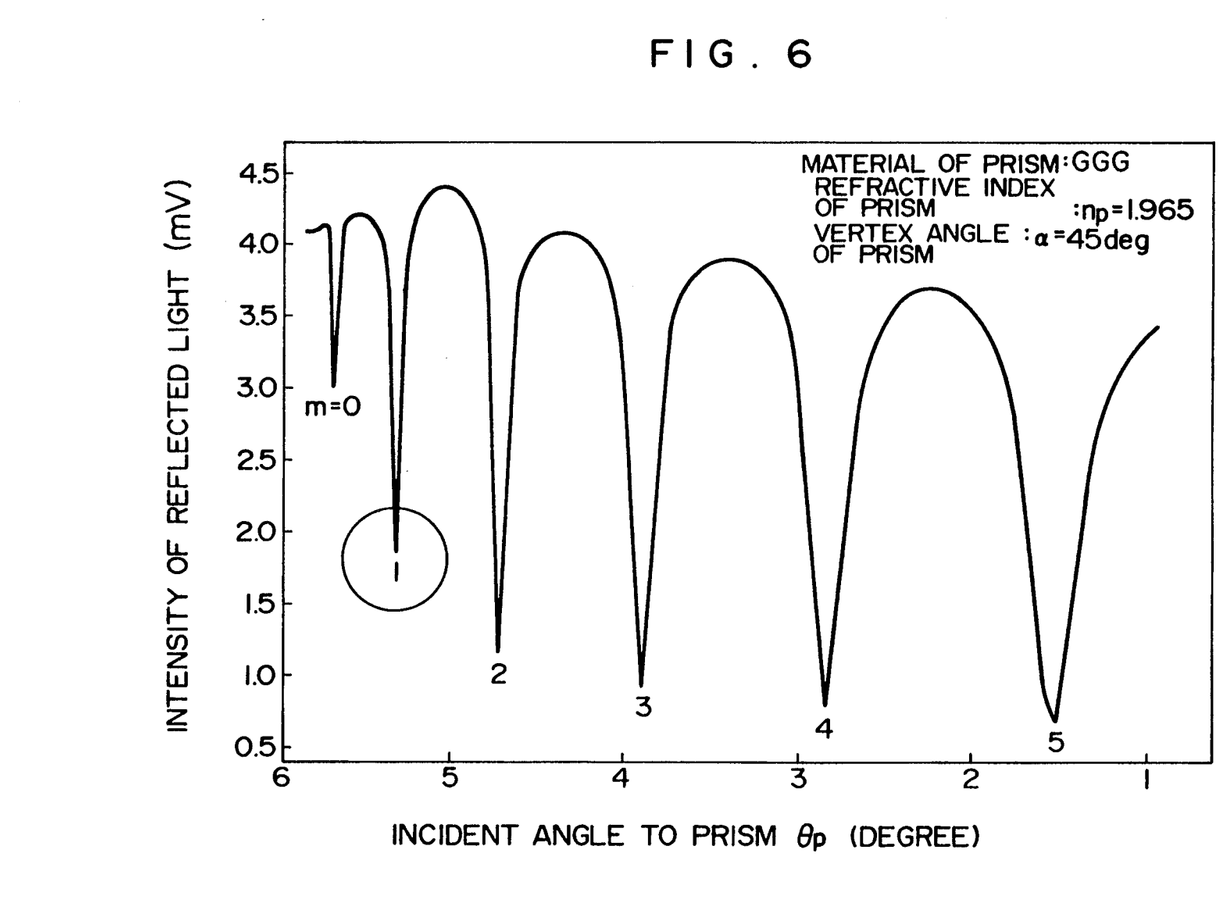
FIG. 6 is another graph showing the relation between the incident angle to the prism and the intensity of the reflected light obtained by means of a photodetector by the measuring method according to the present invention.

FIG. 6 shows an example of the measurement of the

TABLE 1

| Diffusion condition | Mode m | Incident angle $\theta_P$ | Effective refractive index $N_m$ | Transition point $X_t$ (μm) | Result of analysis |
|---|---|---|---|---|---|
| Substrate: | 0 | −12°4'10" | 2.226428 | 2.491774 | Superficial |
| LiNbO$_3$ | 1 | −12°42'39" | 2.219486 | 2.852782 | refractive index |
| Ti Film | 2 | −13°16'23" | 2.213387 | 4.086324 | $n_0 = 2.230740$ |
| thickness: | 3 | −13°41'15" | 2.208883 | 5.366459 | *(2.231304) |
| 100 nm | 4 | −13°57'39" | 2.205909 | 7.186556 | Diffusion |
| Diffusion |   |   |   |   | depth (μm) |
| duration: |   |   |   |   | dx = 4.843248 |
| 20 h |   |   |   |   | *(4.919349) |
|   |   |   |   |   | Predicted values by |
|   |   |   |   |   | diffusion experiment |

The method described above for measuring the distribution of the refractive index can be applied to the measurement of the distribution of the impurity concentration due to impurity diffusion or ion implantation in an Si substrate and the measurement of the thickness of an epitaxially grower layer in various steps for fabricating semiconductor elements, by utilizing infrared ray as Si thermal oxidation film, which is important in fabrication steps for semiconductor devices and optical integrated circuits. The preparation of a sample was effected, as follows. An Si monocrystal 400 μm thick was heated for about 30 hours at a temperature of 1200° C. in a circulating oxygen atmosphere, to which water vapor is added, by means of a quarts tube type electric furnace. In FIG. 6, the abscissa represents the incident angle $\theta_p$ of the laser light beam to the prism and the ordinate the intensity of the light reflected by the bottom face of the prism and measured by the photodetector. Table 3 shows results of the measurement of the incident angle $\theta_p$ corresponding to each of different modes. On the other hand, Table 4 shows results of calculation of the refractive index $n_f$ and the film thickness h of the SiO$_2$ film, obtained by using Eq. (9). In general the refractive index of SiO$_2$ is believed to be 1.46. On the contrary, by the present method a value of 1.458981 has been obtained therefor. The value $n_f$ calculated for each of the modes was so good that the standard deviation thereof was as small as $2.46 \times 10^{-5}$. On the other hand, although the precision of the measurement of the film thickness is somewhat decreased with respect to $n_f$ so that the standard deviation thereof is $3.28 \times 10^{-3}$ $\mu$m, it can be thought that this is a precision sufficient for fabricating optical integrated circuits and semiconductor devices.

TABLE 3

| Mode m | Incident angle $\theta_p$ |
| --- | --- |
| 0 | 5°40'8.5" |
| 1 | 5°18'26.5" |
| 2 | 4°42'27.0" |
| 3 | 3°52'24.5" |
| 4 | 2°48'30.5" |

TABLE 4

| No | Mode m | | Refractive index $n_f$ | Film thickness h ($\mu$m) |
| --- | --- | --- | --- | --- |
| 1 | 0 | 1 | 1.458966 | 4.9348 |
| 2 | 0 | 2 | 1.458967 | 4.9342 |
| 3 | 0 | 3 | 1.458967 | 4.9332 |
| 4 | 0 | 4 | 1.458969 | 4.9299 |
| 5 | 1 | 2 | 1.458968 | 4.9338 |
| 6 | 1 | 3 | 1.458971 | 4.9328 |
| 7 | 1 | 4 | 1.458979 | 4.9297 |
| 8 | 2 | 3 | 1.458978 | 4.9392 |
| 9 | 2 | 4 | 1.458999 | 4.9278 |
| 10 | 3 | 4 | 1.459905 | 4.9245 |
| Average value | | | 1.458981 | 4.9312 |
| Standard deviation | | | $2.46 \times 10^{-5}$ | $3.28 \times 10^{-3}$ |

Furthermore the measuring method described above can be applied to various sorts of thin films such as a photosensitive resin film, a passivation film, etc.

EMBODIMENT 4

Figure 7A:
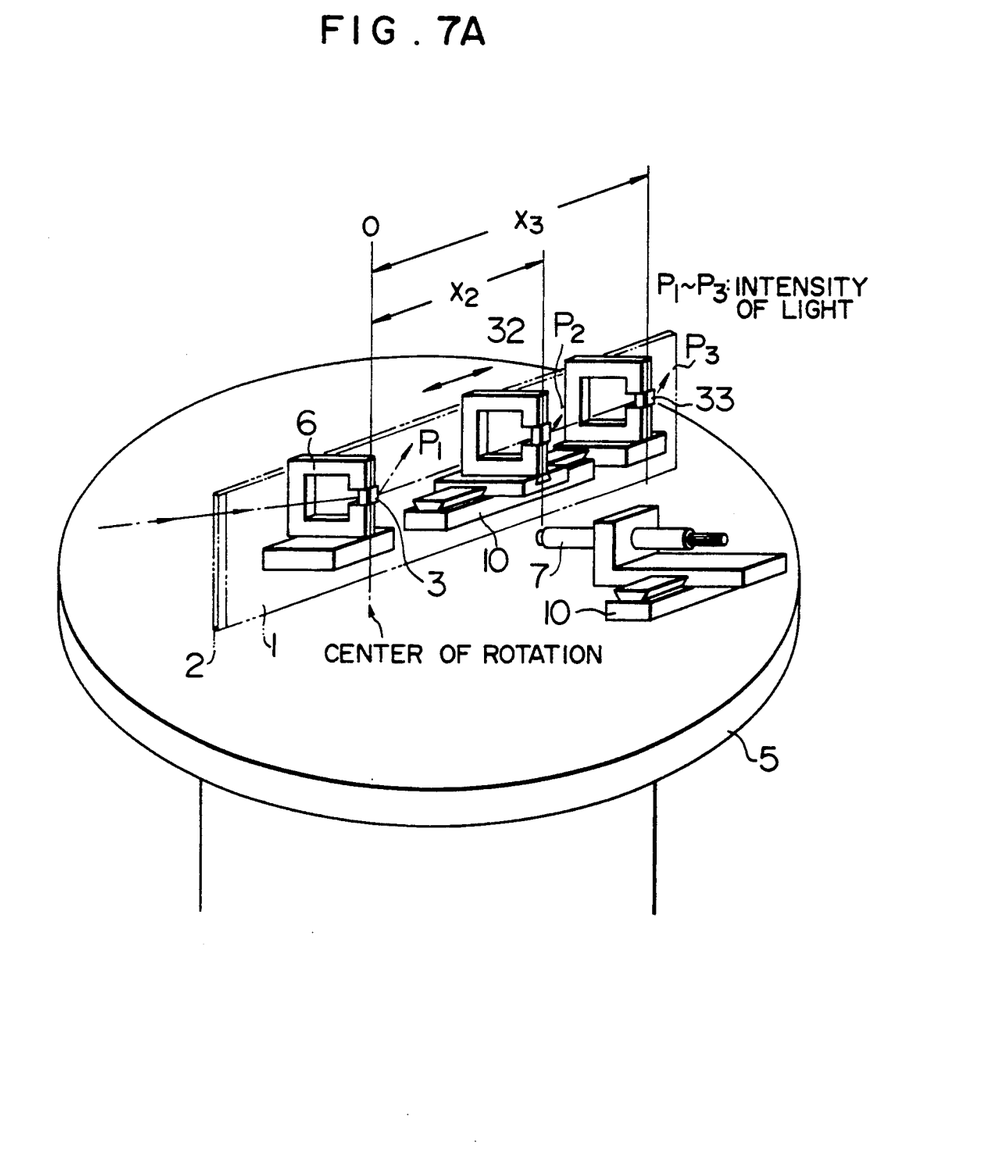
FIG. 7A is a perspective view illustrating another embodiment of the apparatus for measuring the propagation loss in the optical waveguide according to the present invention.
Figure 7B:
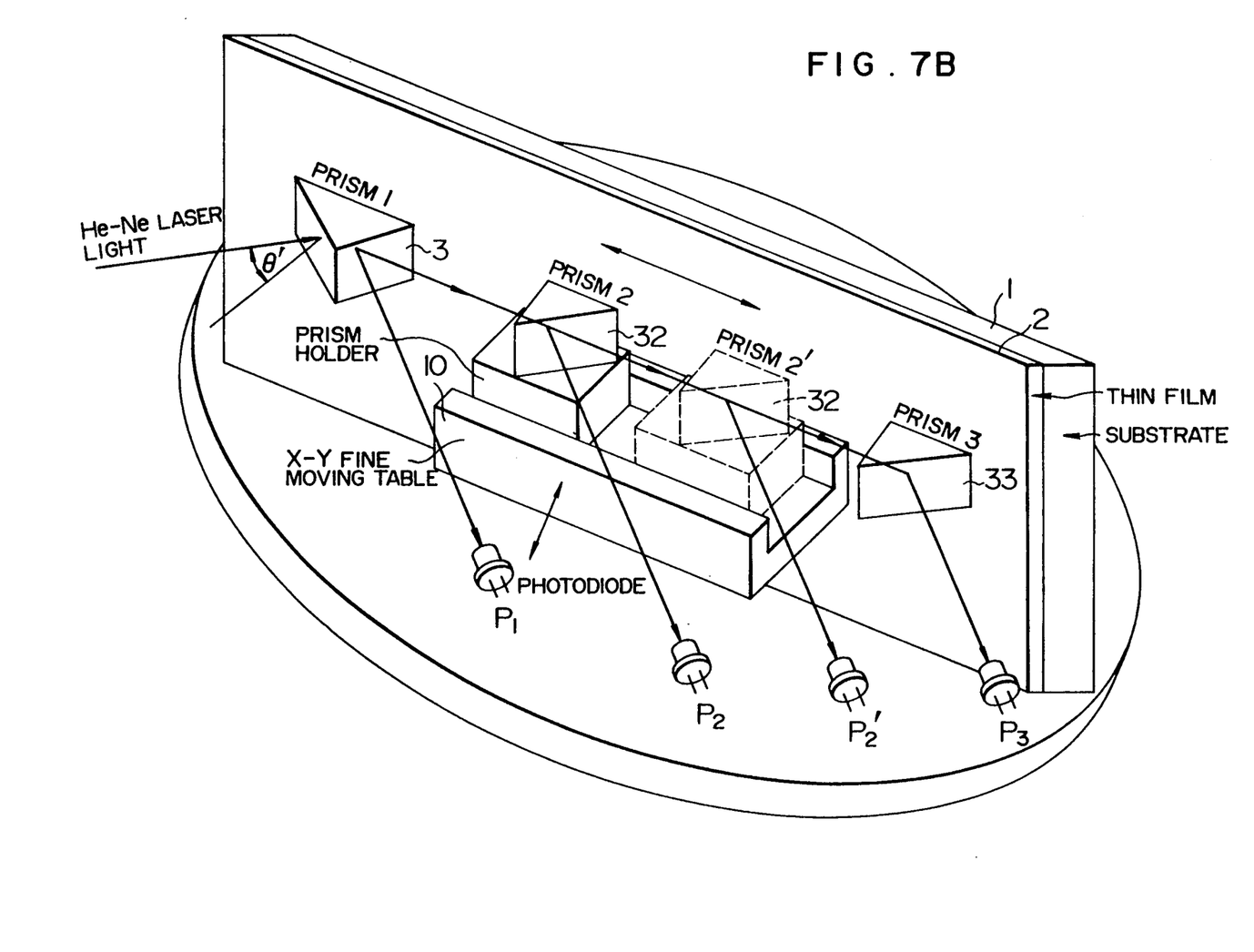
FIG. 7B is a perspective view of the measuring apparatus indicated in FIG. 7A, seen from a different angle.
Figure 8A:
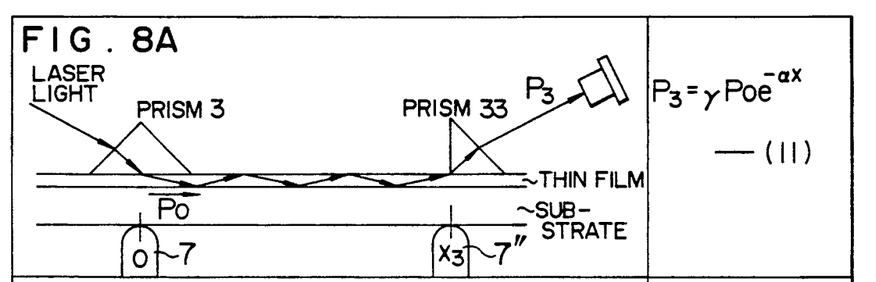
FIGS. 8A to 8C are schemes for explaining the method for measuring the propagation loss and the principle of the measurement.
Figure 8B:
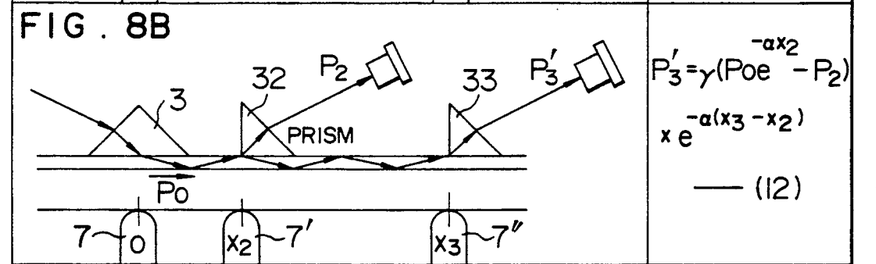
Figure 8C:
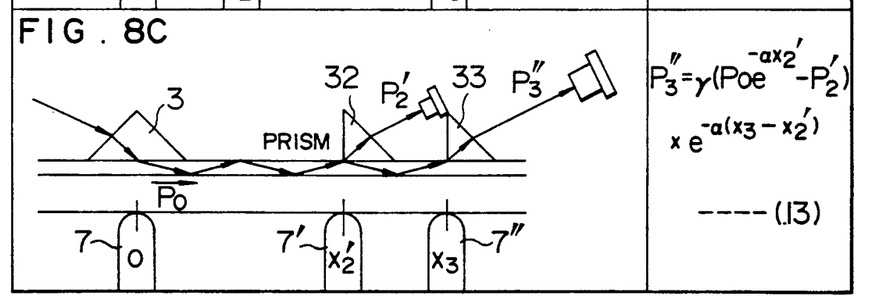

FIGS. 7A, 7B, 8A, 8B and 8C show another embodiment of the present invention, indicating a method for measuring the propagation loss, which is important for fabricating optical integrated circuits, in which FIG. 7 is a perspective view of a device for measuring the propagation loss; FIG. 7B is a perspective view of the measuring device indicated in FIG. 7A, seen from another angle; and FIGS. 8A to 8C are schemes for explaining the method for measuring the propagation loss and the principle thereof. In addition to the basic construction of the device indicated in FIG. 1, the device indicated in FIG. 7A is provided with a movable second prism 32 for taking out the guided light propagating in the optical waveguide 2 and a monitoring third prism 33. Now the method for measuring the propagation loss will be explained in detail, referring to FIGS. 8A, 8B and 8C. In these figures the origin is at the position of the prism 3; the position of the prism 32 is represented by x$_2$; the position after the displacement of the prism 32 by x$_2'$; and the position of the prism 33 by x$_3$. In FIG. 8A, the power of the light guided by the prism 3 to the optical waveguide 2 being denoted by P$_0$, the intensity of the light emitted through the prism 33 by P$_3$, the following equation is valid:

$$P_3 = \gamma P_0 e^{-Lx_3} \quad (11)$$

where $\gamma$: coupling coefficient of the prism 33, and L: propagation loss in the optical waveguide. Next the prism 32 is located at the position x$_2$, the intensity of the light emitted through the prism 32 is denoted by P$_2$ and the intensity of the light emitted through 33 by P$_3'$. Then, $$P_3' = '(P_0 e^{-Lx_2}) e^{-L(x_3 - x_2)} \quad (12)$$

is valid. Further, the prism 32 being moved to x$_2'$, the intensities of the light emitted through the prisms 32 and 33, respectively, being denoted by P$_2'$ and P$_3'$, the following equation is valid;

$$P_3'' = \gamma(P_0 e^{-Lx_2'} - P_2') e^{-L(x_3 - x_2')} \quad (13)$$

Consequently, using Eqs. (11) to (13), the propagation loss L in the optical waveguide 2 is given by:

$$L = \frac{\ln \{P_2'(P_3 - P_3')/P_2(P_3 - P_3'')\}}{x_2 - x_2'} \quad (14)$$

As an example of measurements of the propagation loss described above, L of the Ti diffusion LiNbO$_3$ optical waveguide described in EMBODIMENT 1 was measured. As the result L=0.5 dB/cm was obtained. Further the result was so good that errors of repeated measurements were below 0.5%. By the present method, by disposing the monitoring third prism 33 it is possible to intend to improve the precision of the measurement, because the coupling efficiency of the second prism 32 has no influences on the measurement

EMBODIMENT 5

Figure 9:
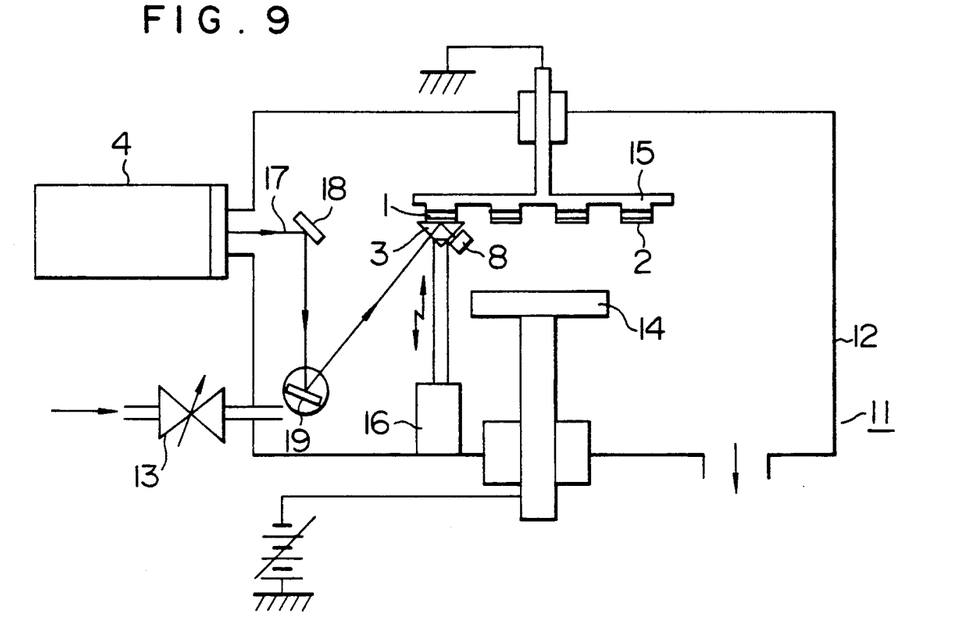
FIG. 9 is a scheme illustrating an apparatus for fabricating thin films provided with the apparatus for measuring the optical constants of the thin film, which is still another embodiment of the present invention.

FIG. 9 illustrates still another embodiment of the present invention, which is a sputtering apparatus 11, an example of a thin film formation device necessary for fabricating optical integrated circuits and semiconductor elements. In FIG. 9, after having evacuated a chamber 12 in vacuum, gas such as Ar etc. is introduced therein through a flow rate regulating value 13. Ar gas is ionized by applying a high voltage between a target 14 and a substrate holder 15 and ions thus produced are collided with the target. In this way, atoms at the surface portion of the target are sputtered by Ar ions and deposited on the substrate 1. At this time, in order to evaluate physical properties and the thickness of the thin film 2 in-situ, the formation of the film is interrupted temporarily and a prism holder 16 having a up and downward moving mechanism is brought into contact with the substrate 1 to be monitored. Next a laser light beam is projected from the exterior of the chamber 12 thereto through mirrors 18 and 19 and the intensity of reflected light is detected by means of a photodiode 8. Here the mirror 19 can be rotated in unit of 0.1 sec by means of a pulse motor (not shown in the figure) to regulate the incident angle to the prism. In this way it is possible to measure the film thickness and the refractive index with a precision as high as $1 \times 10^{-5}$ without taking out the sample in the atmosphere. Further, as described previously (EMBODIMENT 2), since the refractive index of the thin film thus formed is strongly correlated with the conditions of the film formation, it is possible to control the conditions of the film formation by feeding back data obtained by measuring the refractive index thereto and in this way to fabricate the thin film having a stable quality. The present apparatus for forming thin films can be applied not only to the sputtering device but also to various sorts of apparatuses for forming thin films such as a vacuum evaporation device, a CVD device, an ion plating device, etc. Furthermore the present apparatus for forming thin films can be applied to the formation of thin films made of all sorts of materials used in optical integrated circuits and semiconductor elements such as GaAs, InP, $TiO_2$, ZnO, PLZT, $Si_3N_4$, $SiO_2$, etc.

EMBODIMENT 6

Figure 10A:
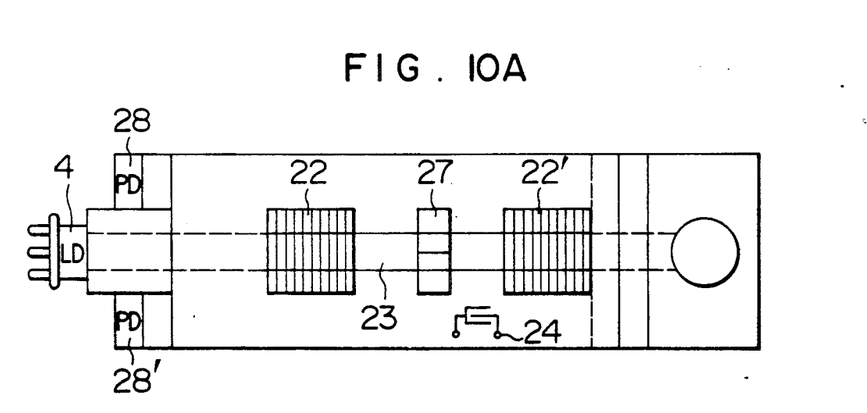
FIG. 10A is a plan view of an optical integrated circuit fabricated while monitoring the optical constants of the thin film, which is still another embodiment of the present invention.
Figure 10B:
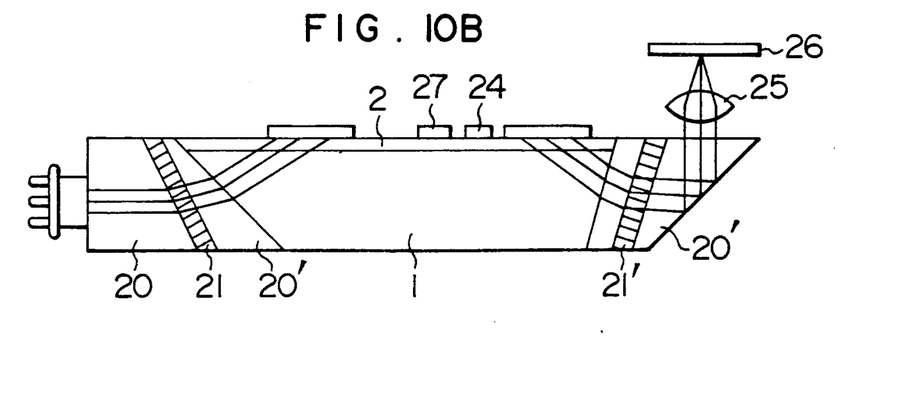
FIG. 10B is a front view of the optical integrated circuit indicated in FIG. 10A.
Figure 11A:
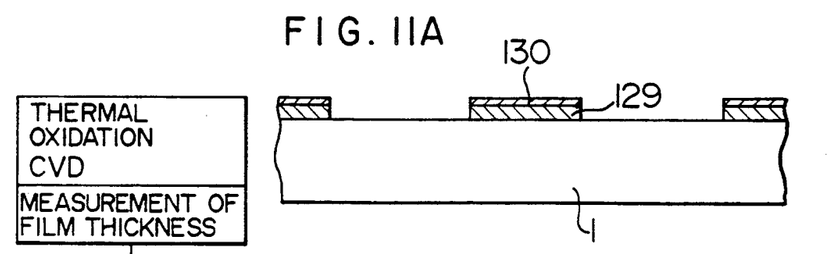
FIGS. 11A, 11B, 11C an 11D show schemes for explaining a process for fabricating the thin film including the process, by which the optical constants of the thin film are monitored, which is still another embodiment of the present invention.
Figure 11B:
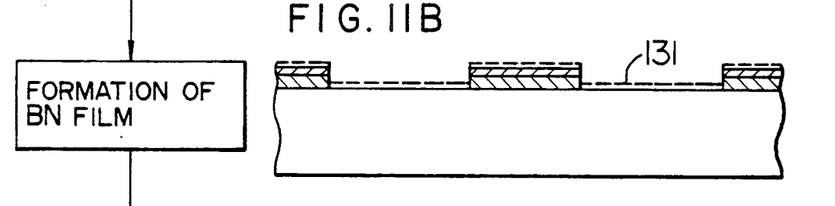
Figure 11C:
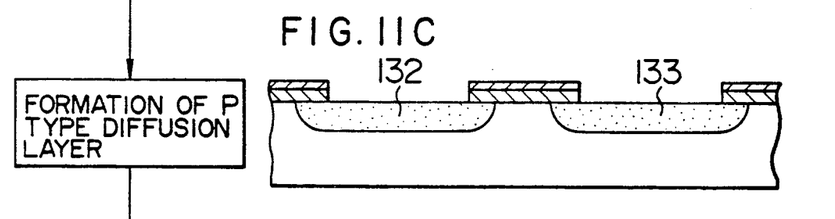
Figure 11D:
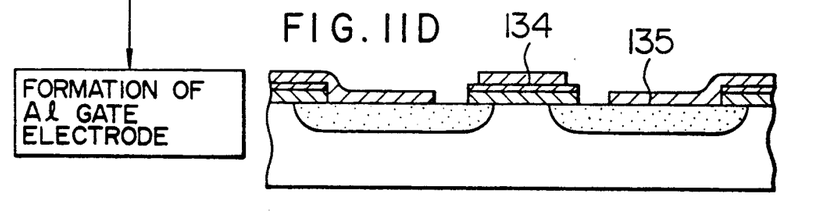

FIGS. 10A and 10B illustrate still another embodiment, which is an example of the application as a process monitor for measuring the refractive index and the film thickness of various sorts of thin films, which are inevitably necessary for fabricating an optical pickup element for an optical disc device, which is taken as an example of the optical integrated circuits. In the optical integrated circuits (OIC) indicated in FIGS. 10A and 10B, a light beam emitted by a semiconductor laser 4 coupled with a glass block 20 is diffracted by a diffraction grating 21, further refracted at the interface between the glass block and the substrate and coupled with an optical waveguide 2 through a grating coupler 22. The guided light beam 23 is deflected by means of an SAW optical deflector 24 and projected to another grating coupler 22' to be diffracted into the substrate. The light diffracted into the substrate is further diffracted by another diffraction grating after having been refracted at the interface between the substrate and the glass block. Then it is reflected at an end surface of the glass block to emerge therefrom upward and collected by a lens 25 having a mechanism moving vertically with respect to an optical disc to be focused on a pit (information) formed on the surface of the optical disc 26. Light reflected by the optical disc 26 is divided into two parts by injecting it in a beam splitter 27 after having passed through the lens 25, the glass block 20' and the diffraction grating 21' and being coupled again with the waveguide by means of the grating coupler 22', which parts are collected on photodiodes 28 and 28' divided into two so that the information represented by the pit is read out.

Hereinbelow a method for fabricating the OIC described above will be described more in detail. An LiNbO$_3$ crystal optically polished was used as the substrate 1 and Ti was deposited thereon to a thickness of 24 nm by sputtering, which was subjected to thermal diffusion to form the optical waveguide 3. The conditions, under which the sputtering described above was effected, were as follows: the high frequency power was 300 W; the pressure of argon gas was 0.35 Pa; and the speed of the sputtering was 0.4 nm/sec. The thermal diffusion was effected by means of an electric furnace in an argon gas atmosphere heated at a temperature of 1000° C. for 2 hours and subsequently oxygen gas was made flow therethrough for 0.5 hour. Here the refractive index of the optical waveguide 2 was measured by the method identical to that described in EMBODIMENT 1. As the result, a superficial refractive index $n_0 = 2.220$ was obtained and it was found that it was a TE single mode waveguide having an effective refractive index $N = 2.209$. It is possible to control the process conditions with a high precision by comparing these measured values with the corresponding optical designed values and by feeding them back thereto.

Next, in order to form various sorts of gratings on the optical waveguide 2, $TiO_2$ was deposited to a thickness of 100 nm by reactive sputtering. The sputtering conditions were as follows: a $TiO_2$ target was used; argon and oxygen were used as the sputter gas; the flow rate ratio of $O_2$ to Ar was 0.7; the pressure of the sputter gas was 0.42 Pa; the high frequency power was 500 W; and the speed of sputtering was 0.1 nm/sec. The thickness and the refractive index of the $TiO_2$ film were measured in the same way as in EMBODIMENT 2.

Then, in order to work finely the $TiO_2$ film in a predetermined grating shape, an ionizing partial sensitive resin film was formed on the $TiO_2$ film by the rotary application method. Here chloromethylated polystylene (CMS-EXR: made by Toyo Soda Co.), which is an electron beam sensitive resin, was used. Here the thickness of the resin film was measured in the same way as described above and a result of 500 nm was obtained. The resin film was irradiated with an electron beam in a predetermined grating shape after having been prebaked at a temperature of 130° C. for 20 minutes. The irradiation was effected under a condition of an electron beam diameter of 0.1 μm and an irradiation dose of 16 μc/cm$^2$. A mask made of the resin was formed by developing it after the exposure by the electron beam. Thereafter the resin film was worked finely so as to form a grating by ion etching. The ion etching was effected under a condition that $CF_4$ was used as the etching gas; the pressure was 3.8 Pa; the high frequency power was 200 W; and the etching duration was 15 min. The resin mask was removed after the etching to form the grating element. For forming the diffraction grating 21 and 21' a substrate made of BK-7 glass was used, on which an $SiO_2$ film about 8 μm thick was formed by the CVD method using $SiCl_4$ and $O_2$ as starting material, the evaporation method, the sputtering method, etc. Next, in order to work the $SiO_2$ film in a predetermined grating shape by the photolithographic method, a photosensitive resin film (OFPR 800) 1 μm thick was formed by the spin coating method. The resin film was subjected to close exposure by means of a UV exposing apparatus by using the photomask, on which the predetermined grating shape was traced. After the exposure it was developed after having been subjected to an immersion treatment in chlorobenzene at a temperature of 40° C. for 5 minutes. A Cr film was deposited on the grating pattern made of the resin by evaporation and a mask made of Cr was formed by removing the resin by ultrasonic cleaning in acetone. Thereafter the $SiO_2$ film was worked finely by ion etching using $CF_4$ gas and the grating pattern was formed by removing the Cr film. This photolithographic technique can be applied also to the fine work of the grating film described above. End surfaces of the substrate 1, on which the elements described above were formed, the diffraction grating 21 and 21' and the glass blocs 20 and 20' made of BK-7 were cut at predetermined angles and polished. Then they were adhered to each other, using an adhesive having a refractive index almost equal to that of BK-7. In this way the optical IC indicated in FIGS. 10A and 10B was formed by coupling a semiconductor laser and a photodiode therewith at end surfaces thereof.

In order to evaluate characteristics of the OIC described above, it was mounted on an optical disk device used exclusively for reading out and search of data was effected. As the result, it was verified that it can be operated approximately as well as designed. Further it was verified that it passes a predetermined endurance test. The process monitor described above for measuring the refractive index and the film thickness in the fabrication of optical integrated circuits can be applied not only to parts for the optical communication but also to various sorts of optoelectronic parts.

EMBODIMENT 7

FIGS. 11A, 11B, 11C and 11D show still another embodiment of the present invention, which is an example, in which an MOS transistor is taken as an example of semiconductor elements and the present invention is applied as a process monitor for measuring the film thickness in fabrication steps for various sorts of semiconductor thin films.

In FIGS. 11A, 11B, 11C and 11D as the silicon substrate 1 a (100) surface n conductivity type silicon wafer was used, whose surface was mirror-polished and whose donor impurity concentration was $1 \times 10^{15}$ cm$^{-3}$ (resistivity 4 to 6 Ω.cm). Then an SiO$_2$ film 129 by thermal oxidation and an SiN film 130 by CVD were formed as a gate insulating film. The thermal oxidation was effected under a condition that water vapor was sent as oxidizing atmosphere and the oxidation was executed for 100 minutes at a temperature of 1000° C. The CVD was effected under a condition that a mixture gas of NH$_3$ 99% and SiH$_4$ 1% was supplied; the temperature of the substrate was 850° C; the pressure in the furnace was 66 Pa and the duration of the deposition was 20 minutes.

Here the thickness of the SiO$_2$ thermally oxidized film was measured in the same way as that used in EMBODIMENT 3 and a result of 600 nm was obtained. Further the thickness of the SiN film was measured in the same way as that used in EMBODIMENT 2 and a result of 500 nm was obtained. In the case where there are fluctuations in the film thickness, it can be controlled with a high precision by feeding back them to the process condition.

Next windows for the drain and source regions are formed. At first photosensitive resin is applied on the whole surface and the parts thereof on the drain and source regions are removed by the usual photolithographic technique. Next windows are formed in the SiN film by the plasma etching method, using the photosensitive film as a mask. Further windows are formed in the SiO$_2$ film, using the SiN film as a mask with an etching solution of HF:NH$_4$F =12:100. Next a BN film 131 is deposited to a thickness of about 1500 nm by the CVD method, using B$_2$H$_6$—NH$_3$ gas at a substrate temperature of 700° C. after having removed the photosensitive film.

Then p conductivity type diffusion layers are formed for the drain region 132 and the source region 133 by a thermal diffusion processing for 6 hours at a temperature of 1150° C. in an N$_2$ atmosphere. Further Al electrodes 134 and 135 are formed on the gate insulating film. The Al electrodes 134 and 135 are formed by the usual photolithographic method and the usual etching technique by working an Al film formed by the vacuum evaporation method in a predetermined electrode shape.

In order to evaluate characteristics of the MOS transistor described above, drain voltage (V$_D$)-drain current (I$_D$) characteristics were measured. As the result it was confirmed that I$_D$ in the saturation region doesn't depend on V$_D$ but it is constant and the saturation characteristics are very good. Further, the process monitor described above in the fabrication of semiconductor elements can be applied to fabrication processes of not only bipolar transistors but also various sorts of microcomputers and memories, apart from MOS transistors.

In the above, the present invention has been explained, using some preferred embodiments. In the measurement of the refractive index of a thin film described above, in the case where the thickness of the thin film is small or in the case where the difference in the refractive index between the thin film and the substrate is small, it is called single mode waveguide, in which only the light, for which the mode number m=0 in Eq. (2), is guided. Consequently the eigenvalue equation (2) for the waveguide mode can form no simultaneous equations and it is presumed that either one of the refractive index n$_f$ and the film thickness h is known.

Therefore, a method for solving the problem described above will be described in detail. The laser device serving as the light source emits generally linearly polarized light. In the linearly polarized light there are known 2 sorts, S polarized light and P polarized light. Further it is known that the refractive index of the medium used as the thin film is slightly different, depending on the polarization described above. Consequently, at the measurement of the refractive index of the thin film described above, the polarization plane of the laser light is rotated to measure the incident angle $\theta_p$, for which the intensity of the light reflected by the bottom face of the prism is smallest, for the incident light beam of each of the S polarized light and the P polarized light. Next the effective refractive index N is calculated for each of the polarized light beams by using Eq. (1). In this way it is possible to measure simultaneously the refractive index and the film thickness, by using Eq. (2), also for the single made waveguide.

As described above, according to the present invention, optical constants (refractive index, film thickness, distribution of refractive index, etc.) of a thin film can be measured with a high precision. Further, by feeding back these measured values to the formation process of the thin film, it is possible to fabricate stably optical integrated circuits and semiconductor elements of high performance with a high reproducibility. Still further, by adding 2 prisms to the method described above for measuring the optical constants of the thin film, since the propagation loss of an optical waveguide can be measured with a high precision, effects can be obtained that the performance of the optical integrated circuits is improved and the optical design can be optimized.

What is claimed is:

1. A method for measuring optical constants of a thin film comprising the steps of:
   disposing a prism having a spherical surface such that the spherical surface is close to the thin film;
   projecting at least one light beam coming from at least one light source to said prism, while varying the incident angle thereof;
   projecting the light beam emerging from the spherical surface of said prism, which is closely disposed to said thin film, to said thin film and at the same time measuring the intensity of the light beam reflected by the spherical surface of said prism to determine the incident angle, for which the intensity of the reflected light beam is minimum;

calculating an effective refractive index including the incident angle, the vertex angle of said prism and the refractive index as parameters by using the measured incident angle; and calculating the optical constants of said thin film and the distribution of the refractive index by the WKB (Wentzel-Kramers-Brillouin) method and the inverse WKB method, based on said effective refractive indices thus measured and calculated for a plurality of propagation modes.

2. A method for measuring optical constants of a thin film according to claim 1, wherein the refractive index is calculated to a measurement precision of better than $1 \times 10^3$.

3. A method for measuring optical constants of a thin film according to claim 1, wherein laser light beams emitted by light sources, having different wavelengths, are used for obtaining the dispersion of the refractive index of said thin film.

4. A method for measuring optical constants of a thin film according to claim 1, wherein laser light beams emitted by light sources, different from each other in the polarization state, are used for obtaining the refractive index of said thin film.

5. A method for measuring optical constants of a thin film according to claim 1, the method further including the steps of:

disposing a second prism and a third prism in addition to said prism as a first prism so that the spherical surfaces thereof are close to the thin film;

taking out light, which has been projected through said first prism into said thin film and which has propagated therein, to the exterior by means of said third prism to measure the intensity of the light;

taking out light, which has been projected through said first prism into said thin film and which has propagated therein, to the exterior by means of said second prism to measure the intensity of the light;

taking out light, which has been reflected by the interface of said thin film, when light, which has propagated in said thin film, is taken out to the exterior by means of said second prism, and has propagated further therein, to the exterior by means of said third prism to measure the intensity of the light;

moving said second prism to a position which is different from that used in the preceding step on said thin film and taking out light, which has been projected through said first prism into said thin film and which has propagated therein, to the exterior by means of said second prism, which has been thus moved, to measure the intensity of the light;

taking out light, which has been reflected by the interface of said thin film, when light, which has propagated in said thin film, is taken out to the exterior by means of said second prism thus moved, and has propagated further therein, to the exterior by means of said third prism to measure the intensity of the light; and calculating the propagation loss of the light propagating in said thin film by using measured values of said intensity of the light.

6. A method for measuring optical constants of a thin film comprising:

a step of disposing a first prism, a second prism and a third prism, the bottom surface of each of which is closely disposed to the thin film;

a step of projecting a light beam coming from a light source through said first prism into said thin film;

taking out light, which has been projected through said first prism into said thin film and which has propagated therein, to the exterior by means of said third prism to measure the intensity of the light;

a step of taking out light, which has been projected through said first prism into said thin film and which propagated therein, to the exterior by means of said second prism to measure the intensity of the light;

a step of taking out light, which has been reflected by the interface of said thin film, when light, which has propagated in said thir film, is taken out to the exterior by means of said second prism, and has propagated further therein, to the exterior by means of said third prism to measure the intensity of the light;

a step of moving said second prism to a position, which is different from that used in the preceding step and taking out light, which has been projected through said first prism into said thin film and which has propagated therein, to the exterior by means of said second prism, which has been thus moved, to measure the intensity of the light;

a step of taking out light, which has been reflected by the interface of said thin film, when light, which has propagated in said thir film, is taken out to the exterior by means of said second prism thus moved, and has propagated further therein, to the exterior by means of said third prism to measure the intensity of the light; and a step of calculating the propagation loss of the light propagating in said thin film by using measured values of said intensity of the light.

7. An apparatus for measuring optical constants of a thin film comprising:

at lest one light source;

a prism including a spherical surface disposed closely to the thin film, which makes at least one light beam coming from said at least one light source propagate in the medium thereof to project it through the spherical surface of said prism disposed closely to said thin film, to said thin film and makes light reflected by the spherical surface of said prism emerge to the exterior of said prism;

a light receiving device integrally formed with said prism, for measuring the intensity of light reflected by the spherical surface of said prism;

holding and driving means for holding said thin film and said prism and varies the relative position between said thin film and said light source; and, calculating control means for controlling said holding and driving means and calculating the optical constants of said thin films on the basis of measured values obtained by said light receiving device.

8. An apparatus for measuring optical constants of a thin film according to claim 7, wherein said optical constants include the distribution of the refractive index.

9. An apparatus for measuring optical constants of a thin film according to claim 7, wherein the radius of curvature of the spherical surface of said prism is closely disposed to said thin film, and is comprised between 150 and 400 mm.

10. An apparatus for measuring optical constants of a thin film according to claim 7, wherein laser light beams having different wavelengths emitted by at least one light source are used in order to obtain the dispersion of the refractive index of said thin film.

11. An apparatus for measuring optical constants of a thin film according to claim 7, for measuring the propagation loss in said thin film, further including:
- a second prism, which is movable, for taking out light, which has been projected by said prism to said thin film and has propagated therein, to the exterior of said thin film;
- a second light receiving device for measuring light emerging from said second prism; and
- a third prism for taking out light, which has propagated in said thin film, to the exterior of said thin film.

12. An apparatus for measuring optical constants of a thin film comprising:
- at least one light source;
- a prism disposed closely to the thin film, which makes at least one light beam coming from said at least one light source propagate in a medium thereof project it through a bottom surface of said prism disposed closely to said thin film, and makes light reflected by the bottom surface of said prism emerge to the exterior of said prism, a radius of curvature of the surface of said prism, which is closely disposed to said thin film, is comprised between 150 and 400 mm;
- a light receiving device for measuring the intensity of light reflected by the bottom surface of said prism;
- holding and driving means which holds said thin film and said prism and varies the relative position between said thin film and said light source; and
- calculating control means, which controls said holding and driving means and calculates the spherical constants of said thin films on the basis of measured values obtained by said light receiving device.

13. An apparatus for measuring optical constants of a thin film comprising:
- at least one light source;
- a first prism disposed closely to the thin film, which makes at least one light beam coming from said at least one light source propagate in a medium thereof to project it through a bottom surface of said first prism disposed closely to said tin film, and makes light reflected by a bottom surface of said first prism emerge to the exterior of said first prism;
- a light receiving device for measuring the intensity of light reflected by the bottom surface of said first prism;
- holding and driving means which holds said thin film and said first prism and varies the relative position between said thin film and said light source,
- calculating control means, which controls said holding and driving means and calculates the optical constants of said thin films on the basis of measured values obtained by said light receiving device;
- a second prism, which is movable, for taking out light, which has been projected by said first prism to said thin film and has propagated therein, to the exterior of said thin film;
- a second light receiving device for measuring light emerging from said second prism; and
- a monitoring third prism spaced from said first and second prism for taking out light, which has propagated in said thin film, to the exterior of said thin film, said second and third prisms suited for determining a propagation loss in said thin film as a result of passing light through said second and third prisms.

* * * * *